United States Patent
Stroop (10) Patent No.: US 11,965,559 B2
(45) Date of Patent: Apr. 23, 2024

(54) BEARING ASSEMBLY

(71) Applicant: ONDAL MEDICAL SYSTEMS GMBH, Hünfeld (DE)

(72) Inventor: Nicolas Stroop, Fulda (DE)

(73) Assignee: Ondal Medical Systems GmbH, Hünfeld (DE)

( * ) Notice: Subject to any disclaimer, the term of this patent is extended or adjusted under 35 U.S.C. 154(b) by 554 days.

(21) Appl. No.: 17/265,409

(22) PCT Filed: Aug. 5, 2019

(86) PCT No.: PCT/EP2019/071057
§ 371 (c)(1),
(2) Date: Feb. 2, 2021

(87) PCT Pub. No.: WO2020/025833
PCT Pub. Date: Feb. 6, 2020

(65) Prior Publication Data
US 2021/0270322 A1    Sep. 2, 2021

(30) Foreign Application Priority Data

Aug. 3, 2018  (EP) .................................... 18187396

(51) Int. Cl.
*F16D 55/02*    (2006.01)
*F16C 41/00*    (2006.01)
(Continued)

(52) U.S. Cl.
CPC ............ *F16C 41/001* (2013.01); *F16D 11/10* (2013.01); *F16D 27/09* (2013.01); *F16D 65/186* (2013.01); *F16D 2121/22* (2013.01)

(58) Field of Classification Search
CPC ........ F16C 41/001; F16D 11/10; F16D 27/09; F16D 65/186; F16D 2121/22
(Continued)

(56) References Cited

U.S. PATENT DOCUMENTS 1,869,876 A * 8/1932 Apple ..................... F16D 55/02
                                                188/18 R
1,968,583 A * 7/1934 Apple ................... F16D 63/004
                                                188/164
(Continued)

FOREIGN PATENT DOCUMENTS

CN          1816704 A      8/2006
CN       101065599 A      10/2007
(Continued)

OTHER PUBLICATIONS

English Translation of International Search Report for PCT/EP2019/071057, dated Oct. 9, 2019, 2 pages.

*Primary Examiner* — Christopher P Schwartz
(74) *Attorney, Agent, or Firm* — Seed IP Law Group LLP (57) ABSTRACT

The invention relates to a bearing assembly (10) comprising at least one first bearing element (12) and a second bearing element (14) which are rotatably connected relative to each other along a common longitudinal axis (14). The bearing assembly (10) comprises a brake device (18) which inhibits the rotation of the two bearing elements (12) relative to each other by means of a frictional force produced by the brake device (18), wherein the brake device (18) has at least one frictional element (20) and at least one clamping device (22), by means of which the frictional element (20) is permanently clamped against one of the two bearing elements (12). The bearing assembly also comprises a coupling device (30) which can be moved between an open state and a closed state. In the closed state, the brake device (18) is engaged, whereby when the two bearing elements (12) rotate relative to each other, the rotation is inhibited by the frictional force produced by the brake device (18), and in the open state, the brake device (18) is disengaged.

13 Claims, 6 Drawing Sheets

(51) Int. Cl.
*F16D 11/10* (2006.01)
*F16D 27/09* (2006.01)
*F16D 65/18* (2006.01)
*F16D 121/22* (2012.01)

(58) Field of Classification Search
USPC .............................. 188/77 R, 77 W, 156–164
See application file for complete search history.

(56) References Cited

U.S. PATENT DOCUMENTS

| | | | | |
|---|---|---|---|---|
| 3,078,972 | A * | 2/1963 | Davis | F16D 67/02 |
| | | | | 192/75 |
| 4,593,796 | A * | 6/1986 | Farquhar | F16D 49/08 |
| | | | | 188/77 R |
| 4,606,444 | A | 8/1986 | Sekella | |
| 4,677,877 | A * | 7/1987 | Anderson | F02B 67/04 |
| | | | | 188/77 R |
| 11,674,556 | B1 * | 6/2023 | Marcus | B25J 9/1641 |
| | | | | 414/751.1 |
| 2003/0038000 | A1 | 2/2003 | Wakisaka et al. | |
| 2005/0236245 | A1 * | 10/2005 | Maurice | F16D 67/06 |
| | | | | 192/17 C |
| 2009/0154865 | A1 | 6/2009 | Neubert et al. | |
| 2014/0144743 | A1 | 5/2014 | Brust et al. | |
| 2016/0223031 | A1 | 8/2016 | Atkinson et al. | |
| 2017/0009804 | A1 | 1/2017 | Garing et al. | |
| 2021/0270323 | A1 * | 9/2021 | Stroop | H02K 7/116 |
| 2021/0356004 | A1 * | 11/2021 | Stroop | F16D 65/186 |

FOREIGN PATENT DOCUMENTS

| | | |
|---|---|---|
| CN | 203285845 U | 11/2013 |
| DE | 102014212844 A1 | 1/2015 |
| DE | 102016124126 A1 | 6/2018 |
| EP | 2 829 762 A2 | 1/2015 |
| JP | H06-26500 U | 4/1994 |
| JP | 11-148520 A | 6/1999 |
| WO | 2014/050513 A1 | 4/2014 |

* cited by examiner

BEARING ASSEMBLY

BACKGROUND

Technical Field

The disclosure relates to a bearing assembly, in particular including a brake device.

Description of the Related Art

In known electromagnetically actuated bearing assemblies, an anchor plate having an attached friction pad is pressed by pretensioned pressure springs against a counter face, for example a pressure plate, in order to inhibit a movement of respective bearing elements to each other. The anchor plate is coupled to a first casing part, which may be denoted as stator, in a rotatably fixed way. The pressure plate is coupled to a second casing part, which may be denoted as rotor, in a rotatably fixed way. The friction pad may here be attached to both the anchor plate and also the pressure plate.

In a braked state, the friction generated by the pressure force of the pressure springs generates a braking torque. The braking torque inhibits any unintentional movement of a carrier arm system, for example, which is held by means of the bearing unit in a movable way at least respectively to one rotational degree of freedom. During an electromagnetic operation of the bearing unit, which may also be denoted as activation, current is applied to a strong electromagnet, which is connected to the stator in a fixed way, for example. The resulting magnetic field acts against the pressure force of the springs and attracts the anchor plate. Thus pressing of the friction pad is ended, and stator and rotor may then be rotated relative to one another using little force. A distinctive feature of this operating principle is that the pressure force, which causes the braking torque, corresponds to the force the electromagnet has to generate for releasing the brake. At a high braking torque, the electromagnet thus has to be dimensioned in a correspondingly strong way, and the currents within a coil of the electromagnet are sufficiently large. In addition, the gap between the electromagnet and the anchor plate is crucial for working at high braking torques, as the magnetic force is considerably reduced when the distance to the magnet increases. This results in high requirements regarding manufacturing accuracy and mounting effort, in particular to keep the gap small. For example, for defining the gap, a fine thread which is complex to manufacture having a small slope between the pressure plate and the casing is provided. Here, the position of the pressure plate at the fine thread is fixed by means of an adhesive, which results in a very difficult maintenance.

A further known design solution for setting or braking a bearing unit is the usage of a resilient pressure hose which is expanded by applying a pneumatic interior pressure. Said expansion leads to a pressure force on rotor and stator, and generates a frictional force at the active surfaces which inhibits the rotational movement. The pressure hose may for example also assume the function of the springs and the electromagnet. Detrimental to this solution is that during movement of a carrier arm system which is supported by means of the bearing unit, an abrasive wear on the relatively moved active surfaces of the pressure hose, which is also denoted as pneumatic hose, occurs, when the brake is not released. Said abrasive wear may lead to leaking of the pressure hose, which is also denoted as brake hose. Thus, a durability of the bearing unit may be short, and/or respective maintenance periods may be short. A similar effect may occur by cracks on the respective crimp locations of the resilient hose, on which it is attached. The maintenance of a defect brake hose is a complex service effort.

A third known design solutions for setting or braking a bearing unit is a friction brake unit, which is not releasable. Here, a permanent braking torque between the rotor and the stator is generated, which may not be released by the operator. Usually, the braking torque is selected sufficiently high, thus a movement of the carrier arm system which is supported by the bearing unit is still possible, however unwanted movements are inhibited in a quite reliable way. In some embodiments said braking torque is not adjustable, is changing according to the ongoing wear of the frictional surfaces, and becomes then no longer correctable.

The bearing units described above are all characterized by a high plurality of variants of parts and assemblies. This also contributes to the fact that maintenance of said bearing units is expensive and complex.

For example, bearing units which may be operated by electromagnets are described in DE 10 2007 013 164 A1 and DE 10 2012 202 366 A1.

From US 2016/223031 A1 a coupling device is known. Here, a clamping device is formed by two brake surfaces which are spring-pretensioned against one another. A casing is not described. At best, a carrier arm constitutes a part of the casing within which a brake device is arranged. A gearing which is aligned in the axial direction is shown.

U.S. Pat. No. 4,606,444 describes a coupling which may be actuated by springs. Here, a clamping device is formed by two brake faces which are spring-pretensioned against one another, and an arrangement within a casing is described. A gearing which is aligned in the axial direction is shown.

DE 102016124126 A1 describes a gear arrangement including an overload coupling and a drive train which may be driven by an electric motor. Here, a clamping device is formed by two brake surfaces which are spring-pretensioned against one another. A casing is not shown or described.

US 2017/0009804 A1 describes a friction sleeve, which configuration does not allow a coupling.

BRIEF SUMMARY

It is an objective of the present disclosure to provide a bearing assembly which overcomes the disadvantages stated above at least in part.

Said objective is solved according to the disclosure by a bearing assembly comprising the features of the independent patent claim. Advantageous configurations of the disclosure are described in the respective dependent claims.

The disclosure relates to a bearing assembly. The bearing assembly may comprise at least one first bearing element and one second bearing element which are rotatably coupled relative to each other along a common longitudinal axis. Furthermore, the bearing assembly may comprise a brake device, which inhibits the rotation of the two bearing elements relative to each other by means of a frictional force generated by the brake device, wherein the brake device has at least one frictional element and at least one clamping device by means of which the frictional element may be permanently clamped against one of the two bearing elements. In addition, the bearing assembly may comprise a coupling device which is adjustable between an open state and a closed state. Here, the coupling device may also be denoted as clutch. In the closed state, the brake device may be engaged, in particular in a force path between the two bearing elements, whereby during rotation of the two bearing elements relative to each other said rotation is inhibited by the frictional force generated by means of the brake device. In the open state, the brake device may be disengaged, whereby the two bearing elements are rotatable relative to each other without being inhibited by the brake device.

The bearing assembly may also be denoted as bearing unit including a shiftable friction braking unit. The bearing assembly may also be configured as a heavy duty bearing unit. In particular, the bearing assembly may be dedicated to medical devices, in particular as bearing for support arm systems, as for example support arms of medical devices in a medical treatment room, as for example a surgery room. By means of the bearing assembly, at least one support arm may be coupled to the ceiling of the room and/or an apparatus for holding medical devices, for example. The bearing assembly may also be used for medical devices.

In the bearing assembly, a frictional force for inhibiting the movement of the two bearing elements relative to each other, and/or the pretension force, which causes a generation of a frictional force during the relative movement are thus permanently provided by means of the brake device. For example, the brake device comprises two frictional surfaces which permanently rest on each other and are pressed against each other, which during a movement of the two bearing elements relative to each other are also moved relative to each other, and thus rub against each other. This way, the frictional force inhibiting the movement is generated. However, due to the coupling device a co-movement of one of the two frictional surfaces with one of the bearing elements may be released, thus the two frictional surfaces do not rub against each other, in case the two bearing elements are moved relative to each other. Therefore the brake device is disengaged from the flow of force between the two bearing elements, and a significantly reduced force is required for moving the two bearing elements relative to each other. In said state, only the usual frictional force of the bearing assembly has to be overcome, for example, which is generated by rolling the respective balls of a ball bearing by means of which the bearing elements are coupled to each other, for example. The brake device may thus be disengaged from the flow of force between the two bearing elements. This may also be denoted as linking of the brake device to the two bearing elements. Correspondingly, the coupling device may also be denoted as link device.

Here, the bearing assembly as a whole provides a number of advantages due to providing the pretension force separately for generating the frictional force inhibiting the relative movement of the bearing elements relative to each other, and the possible engagement and disengagement which may be performed separately, which may also be denoted as activation and deactivation of the brake device. The operation force which is required for releasing the brake effect and the frictional force inhibiting the rotation is independent from the frictional force which may be generated or is desired. Thus, the coupling device may be in particular small, lightweight and cost-efficient, for example, but provides a high frictional force reliably at the same time. Here, a reliable engagement and disengagement is further possible. The frictional force which may be generated is not limited by the technical capabilities of engaging and disengaging the brake device. For example, the frictional force, which may be generated, is no longer proportional to an intensity of the electromagnetic field between an electromagnet and an anchoring plate. In addition, the intensity is no longer proportional to a permeability of the materials used, the coupling strength between an electromagnet and a stator and/or a gap between an electromagnet and the plate which is movable thereby for engaging and disengaging the disc. This way, the brake device may comprise a simple configuration, and nevertheless provide high braking forces. For example, the brake device may comprise a frictional surface, in particular without any particular requirements, which is permanently pretensioned by means of a spring against one of the bearing elements, which may also be denoted as pressing.

In addition, the brake device and thus also the bearing assembly may be especially cost-efficient, as it is no longer required to manufacture a precise gap which is complex to manufacture, in order to ensure a uniform braking torque for a product line. In addition, a fine thread for creating such a gap may be omitted. Furthermore, the generated braking force which corresponds to the inhibiting frictional force during movement of the two bearing elements relative to each other, may also be adjustable during final assembly of the bearing assembly or also at the client site, for example in a hospital. This way, the operator may always recognize or require the same operating force for an engaged brake device.

Further, different kinds of activation of the brake device or engagement of the brake device may be provided without having to extensively modify the design of the brake device itself. In the bearing assembly described above, thus the coupling feature and the provision of the pretension for generating the inhibiting frictional force are not provided and/or impacted by a common part, as for example an electromagnet, in particular regarding the configuration of the bearing assembly. In addition, a wear of the bearing assembly may be especially low. In case, for example, a pneumatic hose is used for adjusting the coupling, it doesn't necessarily contact a part having a frictional surface of the brake device and/or other parts which may be moving relative to one another. Correspondingly, the pneumatic hose is not in contact with a part which is moved relative hereto, which may wear the hose and/or damage it otherwise.

Inhibition of the relative movement of the two bearing elements to each other may require an increased force during movement of the two bearing elements relative to each other compared to a bearing assembly without any inhibition. The bearing assembly may also be inhibited to an extent that it is at least completely fixed regarding the usual operation forces. In this case, the frictional force may be correspondingly high that it may not be overcome by an operator any longer. Preferably, the inhibiting frictional force is dimensioned such that the two bearing elements may still be moved relative to each other by means of a usual force of a user, however an undesired movement, for example an unintended bouncing against a carrier arm, is inhibited or at least significantly reduced.

The frictional force may be generated for example thus, that a clamping element of the clamping device of the brake device is moved together with one of the two bearing elements and/or that the frictional element, which is pretensioned by means of the clamping element, is moved together with the other of the two bearing elements. The clamping element may in particular be a clamping element by means of which a frictional element which is configured as a brake ring is encompassed radially on the outside, and is pressed against an outside of the bearing element, whereby a flow of a frictional force between frictional element or brake ring and bearing element is formed.

The clamping element, which may for example be a clamping collar, may be at least partly accommodated in a recess at the frictional element in the peripheral direction. This way, the clamping element may also axially secure the frictional element. Also, the frictional element may be at least partly received in a recess at one of the bearing elements in a peripheral direction. The frictional element and/or the clamping element may also be axially secured. A movement of said parts along the longitudinal axis may thus be inhibited in a reliable way. Thereby, in particular an axial fixing formed as a fine thread and/or an adhesion may be omitted. This way, the bearing assembly may be in particular cost-efficient, and also particularly easy to maintain. In particular, the bearing assembly may be seamlessly disassembled for maintenance and/or replacement of individual parts.

The frictional element may be coupled to one of the two bearing elements in a closed state of the coupling device in a rotatably fixed way, and may be rotatably disengaged thereof in an open state of the coupling device. Respective bearing elements may for example be formed as casing parts of the bearing assembly which are movably coupled by means of a friction bearing or ball bearing to one another. Respective bearing elements may also be bearing parts itself, as for example, respective rings of a ball bearing or a friction bearing. One of the bearing elements may be formed as a stator, for example. The stator may be mounted to a surgery table, a wall and/or a ceiling of a surgery room, for example. The other of the two bearing elements may respectively be formed as rotor, and may be rotatably fixed thereto relative to the other bearing element.

The complete bearing assembly may be enclosed by a resin cover. The resin cover may protect the bearing assembly against contamination and/or protect the respective user against clamping between the respective movable parts of the bearing assembly. The cover may be formed in two parts in order to enable an easy opening and/or disassembling thereof for a maintenance of the bearing assembly.

The brake device may also be denoted as frictional device or frictional brake device. The clamping force and also the frictional force may be effective in the axial or radial direction relative to the longitudinal axis of the bearing assembly. A frictional element or respective pairs of frictional surfaces may for example be arranged at the outer periphery of one of the two bearing elements, for example, on an outer peripheral surface of the rotor. Alternatively or in addition, pairs of frictional surfaces may also be arranged in the longitudinal direction above or below or in the longitudinal direction on a front surface at one of the two bearing elements.

The bearing assembly provides a coupling device and a brake device which are configured as being functionally separated from one another, and also comprise parts which are separated from each other, in particular at least individually movably parts. The pretension for the frictional force may be generated independently of whether a coupling device is clamped or not between bearing elements, which are rotatable relative to each other, in an open or closed state, and thus the brake device in the force path.

In a further advantageous configuration of the bearing assembly the clamping device is provided to be configured to clamp the frictional element by means of an adjustable pretension force permanently against one of the two bearing elements. Thereby, the frictional force for inhibiting the rotation of the two bearing elements may be adjusted relative to each other. The frictional element may thus be a surface of a clamping element which is pressed against one of the two bearing elements, for example, in order to provide the pairs of frictional surfaces. However, the frictional element may also be a part separate from the clamping element. For example, the frictional element may be an additional frictional part having a high surface roughness in order to be able to provide a high frictional force on a small surface. The frictional element may be clamped by means of the clamping device. At the same time, the frictional element may also be formed as replaceable wear part, thus it is possible to maintain the bearing assembly in an easy and cost-efficient way.

By adjusting the frictional force it may be adapted to the respective needs of a user and/or the respective usage of the bearing assembly. For example, the frictional force may be adapted to a length of a carrier arm of a carrier arm system in a surgery room. Thus, a high frictional force may be defined for a long carrier arm, thus for moving said long carrier arm basically the same force is required compared to a shorter carrier arm, due to the higher lever arm compared to a support of the shorter carrier arm. Hereby, the bearing assembly may provide a support for medical devices which is especially comfortable to use. For example, in case of two adjacently supported carrier arms, it may be prevented that the longer carrier arm on a ceiling is always moving first. In addition, by means of the adjustability, respective manufacturing inaccuracies may be compensated in order to provide the same frictional force for any bearing assemblies despite respective manufacturing inaccuracies.

A further advantageous configuration of the bearing assembly provides that the clamping device clamps a split or unsplit clamping collar, a bent wire, in particular having a thread on both ends thereof and being clamped by a clamping nut, a steel rope which is hooked into a clamping element of the clamping device, a steel rope or steel belt, which is clamped by means of the clamping element, as for example a rocker lever, and/or an endless steel rope or endless steel belt which is arranged around the bearing element in U-shape, and is clamped to a clamping element on the ends thereof. The clamping element for clamping the endless steel rope or the endless steel belt may for example be a screw connection. Also, a clamping collar may be clamped by means of a screw connection. The wire may for example be annularly arranged around one of the two bearing elements. The clamping nut may for example comprise an outer hexagon and/or two female threads, wherein one of the female threads is a right-hand thread, and the other is a left-hand thread. By screwing the clamp nut on the wire at both ends thereof, it may be tensioned by a single clamping nut against a frictional element in a simple way, wherein in particular its two ends may be fastened evenly at the same time. Said parts mentioned have in common that they are simple and cost-efficient, and in addition are at least partly available as cost-efficient standard parts. This way, the clamping device may be configured in a simple and cost-efficient way. In particular, the complex and precisely mounted magnetic actuators for releasing the pretension force may be omitted. Basically, the pretension force does not have to be completely releasable. If required, the pretension force should be adjustable, in order to be thus able to adjust the frictional force, as described above. This is in particular simple for the elements described above, for example, by screwing them more tight or less tight.

A further advantageous configuration of the bearing assembly provides that the bearing assembly comprises a casing, wherein the brake device and/or the coupling device are arranged outside or within the casing. The casing may thus be formed by one or both of the bearing elements and comprise them. Inside and outside may thus be defined relative to the radial direction and the longitudinal axis, for example. The casing may for example also enclose bearing surfaces wherein the bearing elements slide down on each other, balls of a ball bearing and/or respective bearing elements, at least in sections or partially. Thereby, the bearing assembly is well protected against contamination and undesired manipulations. By arranging the brake device and/or the coupling device within the casing and/or within the two bearing elements, the bearing assembly may have an especially compact design. By an arrangement outside of the casing or of the two bearing elements, the brake device and/or the coupling device may be in particular easy to access for maintenance. At the same time, the respective parts of the coupling device and/or the brake device do not have to be adapted to a limited interior room, thus respective standard parts may easily be used.

A further advantageous configuration of the bearing assembly provides that the coupling device comprises in particular a gearing being aligned radially inside of one of the two bearing elements, in particular the bearing element against which the frictional element is not clamped, and comprises a corresponding gearing which is in particular extending on the frictional element radially outside, wherein the two gearings are engaged with one another in a closed state of the coupling device, and are not engaged in the open state of the coupling device. In case the gearing is not engaged, this may also be denoted as released engagement. By means of the gearing, the force path may be reliably closed by means of simple configuration measures, thus the brake device may be engaged in the force path between the two bearing elements which are moved relative to each other. The gearing may thus be easily engaged by arranging teeth on a part which is axially movable in the longitudinal direction. For example, on the bearing element, against which the frictional element is not clamped, an axially movable cover plate may be arranged. Said cover plate may for example be axially guided using respective guiding pins and may be pretensioned by means of respective spring elements, which may for example be arranged on the guiding pins, wherein teeth of the gearing are in engagement with one another, in an axial position. By axially shifting said cover plate, the engagement of the teeth may be released, thus the brake device is disengaged. Preferably, the axially movable part is rotatably fixed to the bearing element relative to the longitudinal axis against which the frictional element is not clamped. For example, the cover plate may be rotatably fixed to the respective bearing element by means of the guiding pins. The guiding pins may here also be denoted as guide bolts.

For the described arrangement of the gearings it follows that they may be radially aligned. Respective tooth crests may be radially aligned towards the outside or inside, for example. In case of an axial gearing, it would however be directed with the respective tooth crests in an axial direction, for example. A radially aligned gearing enables an axially short-built bearing assembly. However, the respective gearings may be indented or expanded by an axial movement of one of the two gearings or of one coupling element including a gearing, and are thus easily engaged or disengaged.

The gearing may be formed extending completely peripheral or also extending only partially in the peripheral direction on the outside and/or the inside. For example, on the frictional element an outer annular completely peripheral gearing may be provided, while at the bearing element, to which the frictional element is not clamped, an inner radially only partially extending peripheral gearing is arranged, for example on the cover plate. This way, an engagement may be achieved any time, independent of the angular position of the two bearing elements, while it is not required to provide two completely peripheral gearings. This way, the bearing assembly may be in particular lightweight and cost-efficient. In addition, respective manufacturing tolerances in the gearings may have less demanding requirements, as it is not required to ensure corresponding fittings by using a ring extending completely around the periphery. The coupling may be closed or released by the gearing, thus also a flow of force may be generated or may be released by means of the brake device.

A gearing may be interpreted thus that a part or a portion comprises an outer tooth-shaped surface which may be brought in a force-fitting engagement with the corresponding gearing or the tooth-shaped surface. However, the gearing may here also denote only one such tooth-shaped surface or teeth on one side of the gearing. The force-fitting engagement of the two gearings may also be denoted as gearing engagement.

In a further advantageous configuration of the bearing assembly it is provided that at least one of the two gearings are arranged in a coupling element which is movable in a longitudinal direction. The gearing may be engaged or disengaged and/or moved by moving the coupling element in the longitudinal direction, whereby the coupling is adjustable between the closed and the open position thereof. Such a coupling device is in particular simple and in particular robust. For example, a coupling ring may be provided which is connected to the bearing element, against which the frictional element Is not clamped, in a rotatably fixed, but axially movable way. The coupling ring may in particular be rotatably guided along with said bearing element, for example by means of a plurality of guide bolts which are spaced in the peripheral direction.

A further advantageous configuration of the bearing assembly provides that the coupling device remains in the closed state thereof when not actuated, in particular by pretensioning the coupling device by a spring element in the closed state. A start position of the coupling device to which it automatically returns may also be the closed state thereof. The spring element may here also be part of the coupling device, for example. For example, the coupling ring may be pretensioned in a predetermined axial position by means of spring elements which are attached to respective guide bolts, where the gearing is engaged. For example, said axial position may be preset by the respective abutments, as for example, respective heads of the guide bolts.

The coupling device may be adjusted from the closed state to the open state by operation, in particular by operating an actuator, and automatically return to the closed state after completing the operation. Hereby it may be achieved that the bearing assembly is always inhibited in a movement of the two bearing elements relative to each other, in case the coupling is not operated and/or has failed. This enhances security, as respective bearings are not allowed to be moved in an unrestrained way despite using only a little force.

Advantageously, the relative movement of the bearing elements to each other is not completely blocked by the brake device, thus the carrier arms including the medical devices attached thereon may further be moved, also in case of power outage and/or failure of an actuator in a surgery room, for example. By operating the actuator, that is, in case of no failure, the movement force may thus be significantly reduced by disengaging the brake device, thus the two bearing elements may be moved fast and with little force relative to each other.

Respective spring elements may for example be formed as a pressure spring by means of which a coupling element is pretensioned in a position against an abutment which corresponds to the closed state of the coupling. Respective spring elements may for example be formed as tension spring, coil spring, cup spring, pneumatic spring, hydraulic spring or any other spring element. Preferably, the spring element may store potential energy during adjustment from the closed state into the open state, and use said energy for the subsequent automatic return to the closed state.

A further advantageous configuration provides that the coupling device comprises an electromagnetic actuator, as for example an electromagnet or a solenoid, a drive element as a servomotor, a Bowden cable, a hydraulic actuator and/or a pneumatic actuator as a pressure hose which may be pressurized, and is thus expandable for adjustment between the closed and the open state. The servomotor may also be formed as a step motor, thus an abutment element for defining the respective position for the opened and closed states may be omitted. By means of the actuators mentioned above, the coupling may be operated in simple way, for example in response to a sensor signal, for example a touch sensor on a carrier arm, and/or an operation of an input device, as an operating button. The actuator may be a common standard part which may also be denoted as a catalog item.

Thus, the actuator has not to be configured to provide a respective pretension force for providing the frictional force for inhibiting the movement of the two bearing elements relative to each other and/or releasing it. This way, an especially small, lightweight and/or cost-efficient actuator may be used. The actuator may be selected and formed independently from the actual braking feature of the bearing assembly. An actuator may also be denoted as actor. For example, an electromagnetic actuator may comprise a ring magnet. For example, the pressure hose may cause an engaged and/or closed state of the coupling in a released state, and a disengaged or open state of the coupling device in an expanded state. This way, the coupling device may automatically return to the closed state even in case of a damage of the pressure hose.

A further advantageous configuration of a bearing assembly provides that the coupling device comprises a transmission device by means of which a force for adjustment between the open and the closed state may be transferred and/or a pretension force of the clamping device may be transferred, wherein the transmission device comprises in particular two wedge elements which slide down against each other during adjustment. The transmission device may thus be part of the coupling device, in particular as translation for its actuator and/or the clamping device, in particular as clamping element. Correspondingly, also more than one transmission devices may be provided.

By means of the transmission device, a rotational torque of an actuator may be increased, thus smaller and/or standard actuators may be used for adjustment between the open state and the closed state. This in particular advantageous for the quite small required adjustment paths. For example, during adjustment only respective gearings have to be disengaged which extend only a few millimeters in the longitudinal direction. When altering the pressure, which is used to press the frictional element, sometimes even smaller adjustment paths may be required, but very high forces have to be applied. By sliding of the respective wedge elements on the wedge surfaces along one another, they may move to one another or move away from each other. The wedge elements may here change a distance of the centers thereof to one another, whereby an extreme translation in small space is enabled. In particular, a very high rotational torque may be achieved, whereby the coupling may also be reliably engaged in case of high impacts of frictional forces, and/or high adjustment forces or said engagement may be released again. Also a high pressure of the frictional force for generating a high frictional force may thus easily be provided. In particular, despite the required high pressure, the clamping device may still be adjusted manually and/or by means of simple tools, as for example a screwdriver. For example, the wedge elements may comprise two ring elements rotating relative to each other in the longitudinal direction, which comprise wedge-shaped portions on the sides facing each other, which slide down on each other. This way, the distance between the rings may be adjustable by rotation.

Further features of the disclosure become apparent from the claims, the exemplary embodiments and the figures. The features and the combination of features mentioned in the specification above and the features and combinations of features mentioned in following exemplary embodiments may be used not only in the respective specified combination, but also in other combinations within the scope of the disclosure.

BRIEF DESCRIPTION OF THE SEVERAL VIEWS OF THE DRAWINGS

Here shows.

DETAILED DESCRIPTION

Figure 1:
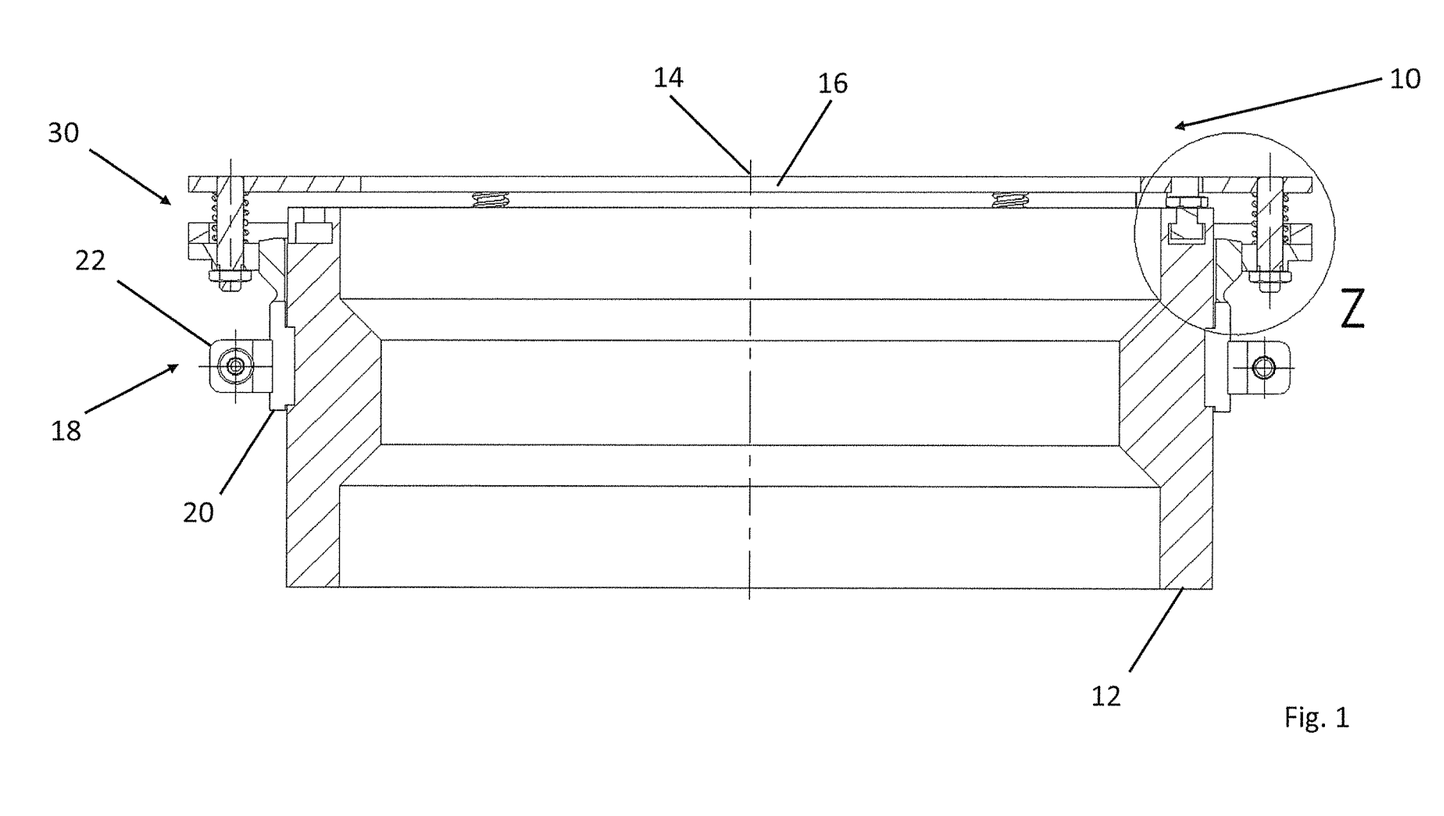
FIG. 1 in a schematic section view a bearing assembly comprising a brake device and a coupling device.

FIG. 1 shows in a schematic section view a bearing assembly 10, which comprises a first bearing element 12, which is embodied as a rotor in the present embodiment. Further, the bearing assembly 10 comprises a second bearing element which is rotatable relative hereto about the longitudinal axis 14, which is configured as stator in the present embodiment and is not shown in FIG. 1. In addition, the bearing assembly comprises a cover plate 16 which is connected to the stator in a rotatably fixed way.

Figure 3:
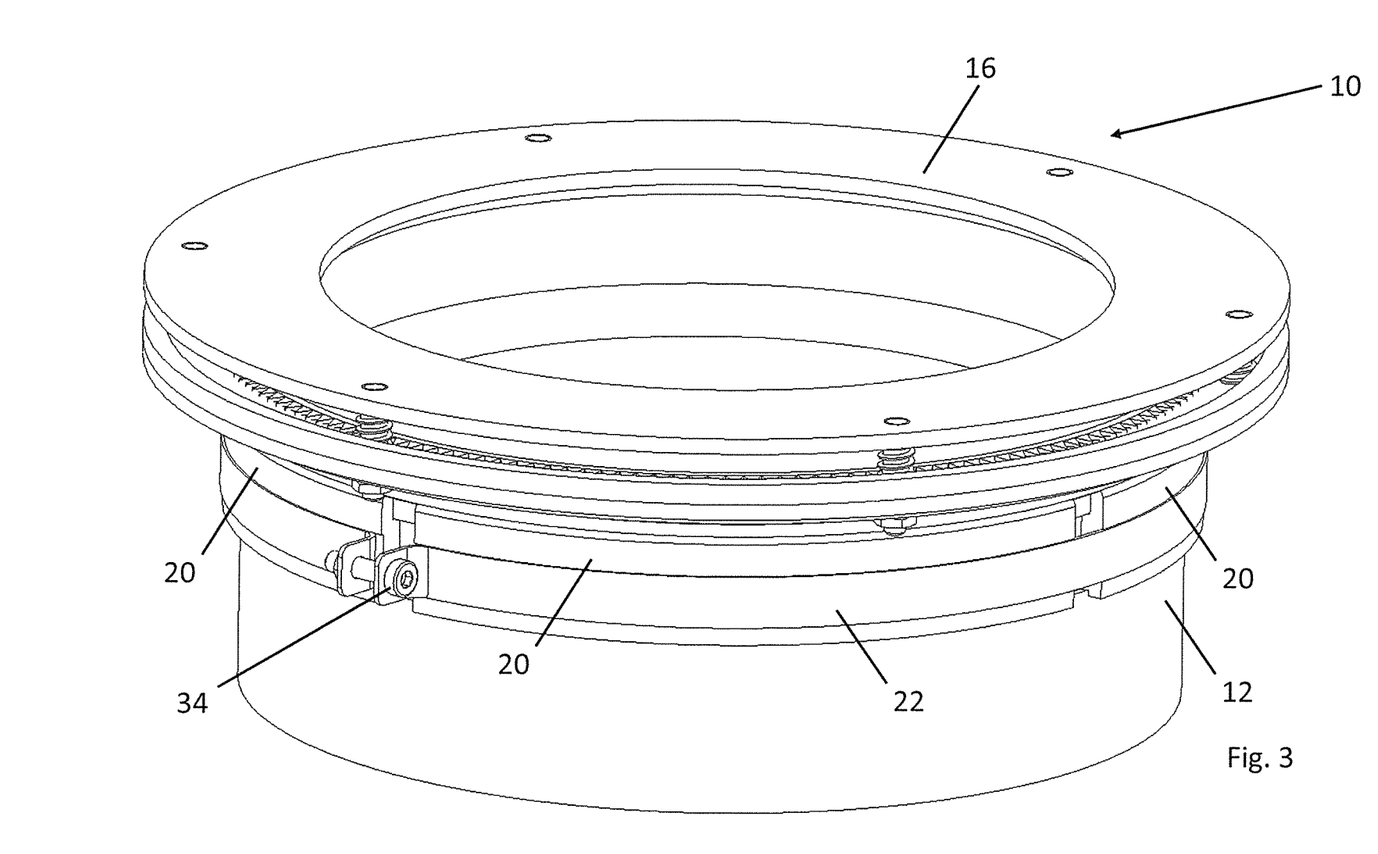
FIG. 3 in a schematic perspective view the bearing assembly according to FIG. 1.
Figure 4:
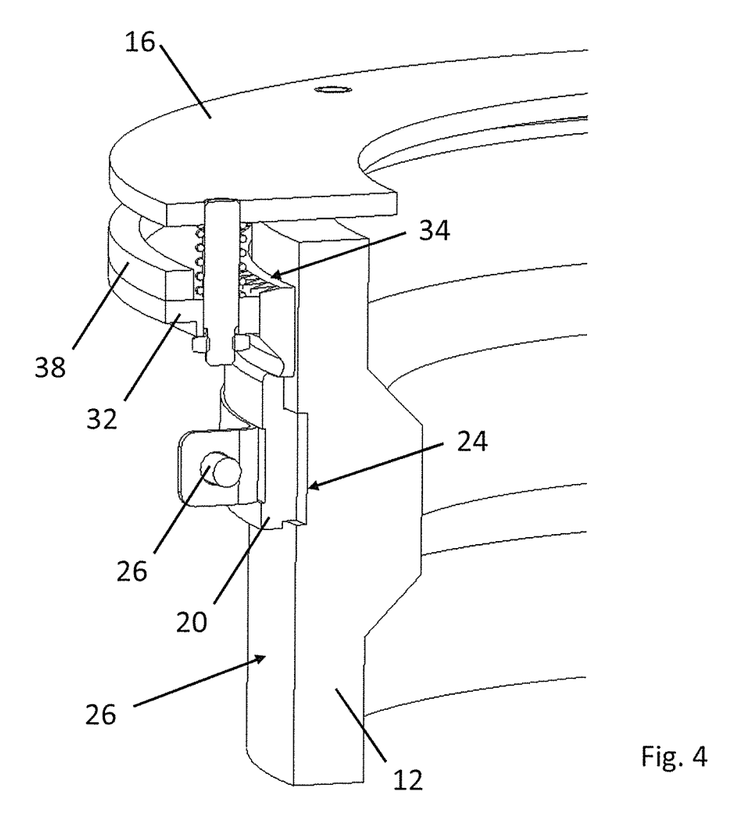
FIG. 4 in a schematic section view a portion of the bearing assembly according to FIG. 3.

Further, the bearing assembly 10 comprises a brake device 18, which comprises a brake ring 20, and a clamping collar 22. As in particular is shown clearly in the schematic perspective views of FIG. 3 and FIG. 4, wherein the bearing assembly 10 is shown only as cutout and sectioned in FIG. 4, the brake ring 20 is thus at least partly accommodated by means of the clamping collar 22 in a radially peripheral recess 24 of an outer peripheral surface 26 of the bearing element 12. This way, the brake ring 20 is axially fixed and may not be moved along the longitudinal axis 14. As is further shown in FIG. 3, the brake ring 20 consists of a plurality of pieces, thus it is easy to mount and disassemble. The brake ring 20 may thus be a wear part or comprise wear parts, which are abrased during generation of a frictional force. Therefore, the clamping collar 22 clamps a brake ring 20 permanently against the bearing element 12, and may also be denoted as part of the clamping device. For the purpose of clamping, the clamping collar 22 may be contractable by means of a screw connection 28 in order to increase or reduce the pretension, and to press the brake ring 20 thus stronger or less strong against the bearing element 12. This way, a respective frictional force may be adjusted, which is generated, in case the rotor and the stator of the bearing assembly 10 are rotated relative to each other about the longitudinal axis 14. Here, said frictional force acts against said rotation, which may also be denoted as braking or inhibiting the rotation.

The brake device 18 or the brake ring 20 may thus be connected to the cover plate 16, whereby the brake ring 20 is moved relatively to the bearing element 12 about the longitudinal axis 14, in case the rotor or bearing element 12 rotates relative to the stator. The brake ring 20 may for example stay in the same position like the second bearing element, which is shown, if the bearing element 12 rotates about the longitudinal axis 14. This way, due to the brake ring 20 which is clamped against the outer peripheral surface 26 of the bearing element 12, a braking force is generated between the respective faces which are here pressed one against the other, which inhibits the rotation. Thus, an increased force for moving the rotor is required. This is for example useful in case a carrier arm of a support device for medical devices is connected to the rotor. This way, medical devices may be moved in a precise and reliable way, in addition, the bearing assembly 10 may thus remain in a respective position without exerting a force on the medical devices and/or against gravity. At the same time, the frictional force may be adjusted in a way that any undesired movement, for example an unintended bouncing against the carrier, is significantly reduced or may even be completely inhibited.

Figure 2A:
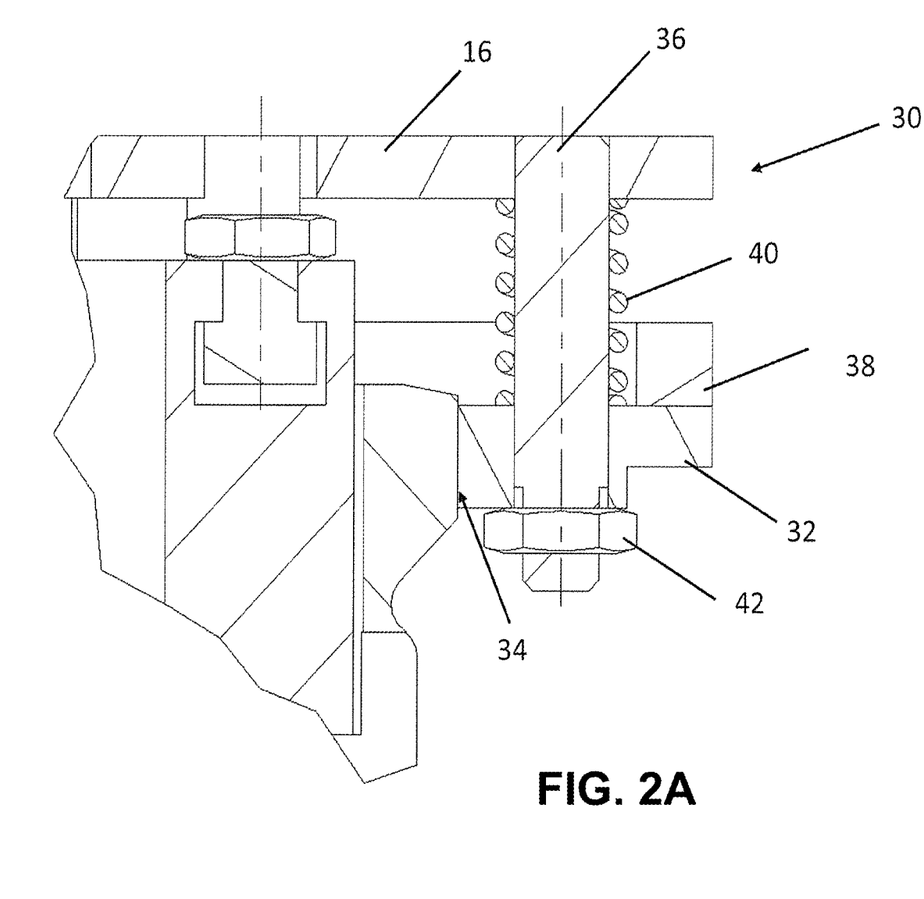
FIG. 2A in a detailed section view a portion of the bearing assembly according to FIG. 1 in a closed state.

Sometimes however a fast movement by leveraging little force is desired. In said case, a coupling device 30, which is especially shown in detail in FIG. 2A and FIG. 2B, which represents the enlarged cutout designated by Z of FIG. 1, may be adjusted between the open state (FIG. 2B) and the closed state (FIG. 2A). The coupling device enables thus to switch the braking function on and off. In FIG. 2A the closed state is shown, respectively. In the closed state, the brake device 18 is engaged, whereby during rotation of the rotor relative to the stator, the movement of the rotor is inhibited by the frictional force generated by the brake device 18. The frictional force which has been generated by the brake device 18 also acts against rotation. A flow of force between the cover plate 16 and the bearing element 12 is thus closed by the coupling device 30. For this purpose, the coupling device 30 comprises a coupling ring 32, which comprises a gearing on the portion 34 radially inside, which is engaged in a gearing extending radially outside of brake ring 20. The gearings are also aligned in the radial direction. An engagement may here be provided only on one peripheral surface, or may be formed by completely peripheral gearings.

Figure 2B:
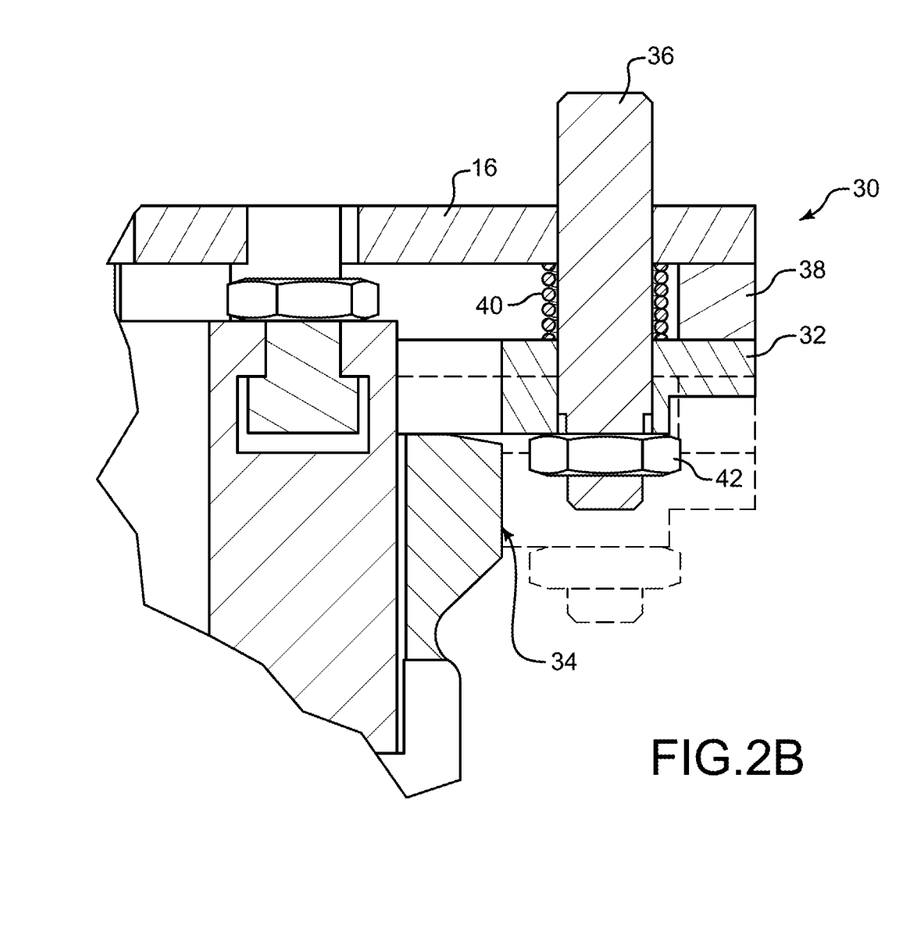
FIG. 2B in a detailed section view of a portion of the bearing assembly according to FIG. 1 in an open state.

In case the coupling device 30 is to be adjusted to the open state, as shown in FIG. 2B, the engagement of the respective gearings has to be released. In the present example, the coupling ring 32 has to be moved along the longitudinal axis 14 upward in the longitudinal direction. For this purpose, the coupling ring 32 is rotatably fixed, however axially movable mounted to the cover plate 16 using the respective guide bolt 36. However, the guide bolts 36 may also be directly mounted to the stator, thus a cover plate may be omitted. Further, the coupling device 30 comprises hereto an electromagnet 38. The electromagnet 38 is coupled to the coupling ring 32. In case of activating the electromagnet 38, for example by applying an electric voltage, the electromagnet 38 is pulled by the thus generated magnetic force together with the coupling ring 32 to the cover plate 16. Hereby, the coupling ring 32 is moved along the longitudinal axis 14 upwards, whereby the engagement of the gearing in the portion 34 is released. In the thus generated open state, the brake device 18 is disengaged, whereby the rotor may be rotated without being inhibited by the brake device 18 relative to the stator around the longitudinal axis 14. Said rotation will then be only inhibited insofar as respective other frictional forces may exist in the bearing assembly 10. For example, a certain inhibition may be generated by rolling down and/or sliding down of respective balls of a ball bearing or respective sliding faces of bearing assembly 10. In the open state, the rotor may be moved relative to the stator in a fast way and with little force.

Due to security reasons, in particular during usage of the bearing assembly 10 in a surgery room for supporting respective medical devices by means of carrier arms supported by using the bearing assembly, the coupling device 30 is pretensioned in the closed state thereof. The bearing assembly 10 or the coupling device thus automatically returns to the close state as soon as the electromagnet 30 is deactivated. Hereto, the coupling device 30 comprises respective pressure springs 40 which are arranged on or at the respective guide bolts 36. By said positioning of the pressure springs 40, they are also supported by the guide bolts 36 and are in addition accommodated in a particular space-saving way. By means of the pressure springs 40, the coupling ring 32 is pressed against respective nuts 42 which are fitted onto the guide bolt 36. The respective nuts 42 serve here as abutment and specify a position for the closed state, in which the respective gearings of the coupling ring 32 and the brake ring 20 are engaged with each other in the portion 34. Preferably, the respective pressure springs 40 are dimensioned in a way that the coupling device 30 remains in the closed state independent of its position and also against gravity.

In the bearing assembly 10, the operation force which is required for releasing the brake effect is independent of the set pretension for generating the frictional force. Thus, for disengagement, the pretension, which acts on the brake ring 20 which is configured as friction element having the clamping collar 22, has not to be overcome. In addition, the pretension does not have to be suspended or released. Instead, for example only the spring force of the respective pressure springs 14 and a friction of the gearing in the portion 34 has to be overcome. The forces, which are required for disengaging the brake device 18, may thus be substantially smaller. Correspondingly, a very small and cost-efficient electromagnet 38 may be used, for example.

At the same time, respective effectively acting dimensions of the respective pairs of brake surfaces, that is the clamped surfaces between brake ring 20 and bearing element 12, may be configured independently of the coupling device 30. Hereby, a high brake torque may be achieved by the same pressure force, or by a smaller pressure force the same brake torque as in a bearing assembly, in which only small surfaces are available for generating the frictional force in a region of a coupling device. For a large surface, and correspondingly hereto only a small pressure for generating an otherwise identical brake torque, the abrasives wear of the brake device 18 may be especially low. As the coupling device 30 itself is not required for generating the inhibiting frictional force, it may be consist of cost efficient and lightweight parts, for example, of resin parts. The coupling device is subjected to only little wear during engagement and disengagement and is not further worn by the actual generation of the frictional force. Therefore, the gearing may be formed as a resin gearing, for example, while a high frictional force may still be achieved due to the pretension using a metal clamp collar 22.

The brake force which may be generated is not limited by the technical capabilities to open or disengage the coupling device 30. In particular, no precise gap has to be provided between the electromagnet 38 and the cover plate 16, in order to keep to a predefined brake torque, as the electromagnet 38 does not specify the inhibiting frictional force by itself. The generated frictional force may be simply adjusted by a user by rotating the screw connection 28, for example by means of a screwdriver. Basically, a plurality of actuators having different active principles may be used instead of the electromagnet 38 for adjusting the coupling device 30.

In addition, as is shown in the figures, the coupling device 30 and also the brake device 18 are arranged radially outside of the bearing element 12. Thus, for example, the screw connections 28 is particularly well accessible for adjustment of the pretension and thus a simple setting of the inhibiting frictional force. In addition, the brake ring 20 is easily accessible, thus it may easily be replaced in case of wear. Due to the screwing connection 28, the pretension force may be easily re-adjusted after occurrence of wear of the brake ring 20, thus the inhibiting brake force is not necessarily reduced by abrasion in the course of time. Also, the coupling device 30 is thus easily accessible for maintenance. In addition, the respective parts of the brake device 18 and the coupling device 30 may be standardized, as the mounting space is barely limited from outside. Respective parts, outer parts have to be only slightly adapted to the available mounting space.

However alternatively, the coupling device 30 and/or the brake device 18 may also be arranged relative to the longitudinal axis 14 radially inside to the bearing element 12 and/or the stator and/or the cover plate 16. This way, the coupling device 30 and/or brake device 18 are well protected against undesired manipulations, damages and/or contamination. In addition, it may thus be prevented that a user pinches his/her finger in a gap of the coupling device 30, without requiring any additional enclosure or casing. In addition, the bearing assembly 10 may thus be in particular small. The bearing element 12 may here also be formed as a part of the bearing casing as well as the stator and/or the cover plate 16.

Figure 5:
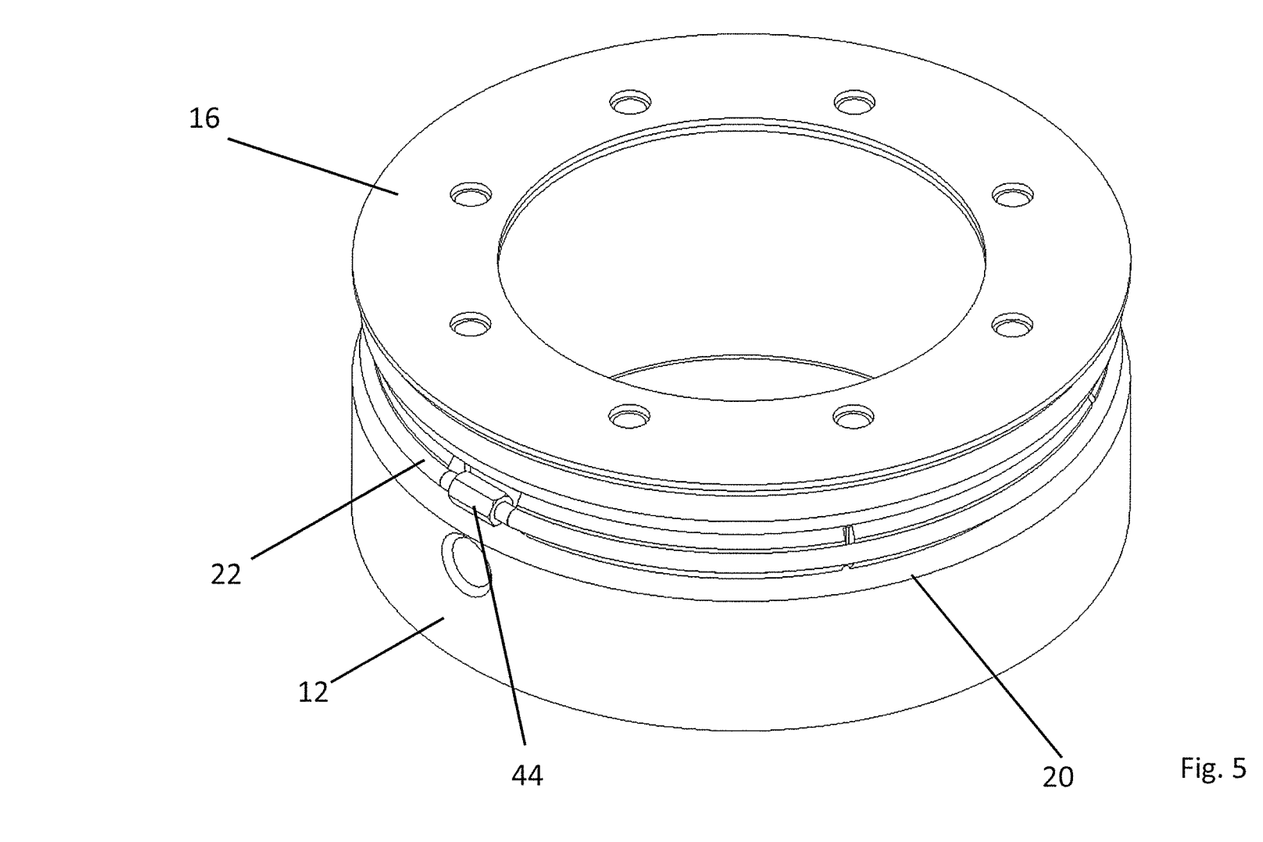
FIG. 5 in a schematic perspective view a further exemplary embodiment of the bearing assembly.

FIG. 5 shows in a schematic perspective view, a further exemplary embodiment of the bearing assembly 10. The clamping device 22 is here designed in a different way. Instead of a steel belt including the screw connection 28, a wire is used for tensioning the brake ring 20, which comprises opposite threads on both ends thereof, and a thread nut 44. Here, the thread nut 44 comprises the respective female opposite threads, thus the wire may be evenly contracted or released on both ends. On the outside, the thread nut 44 is formed as hexagon, thus it may be easily be rotated using a respective wrench for adjusting the pretension force. In said embodiment, the brake ring 20 comprises a peripheral recess in order to axially fix the wire. The wire may for example comprise a thickness of 5 mm to 9 mm.

LIST OF REFERENCE NUMBERS

10 Bearing assembly
12 Bearing element
14 Longitudinal axis
16 Cover plate
18 Brake device
20 Brake ring
22 Clamping collar
24 Recess
26 Outer peripheral surface
28 Screw element
30 Coupling device
32 Coupling ring
34 Portion
36 Guiding pin
38 Electromagnet
40 Pressure spring
42 Nut
44 Threaded nut

The invention claimed is:

1. A bearing assembly comprising at least one first bearing element and one second bearing element which are rotatably coupled relative to each other along a longitudinal axis, wherein the bearing assembly comprises:
   a brake device, which inhibits relative rotation of the at least first and second bearing elements to each other by a frictional force produced by the brake device, wherein the brake device has at least one frictional element and at least one clamping device by which the frictional element is permanently clamped against one of the at least first and second bearing elements, and
   a coupling device which is adjustable between an open state and a closed state,
   wherein in the closed state the brake device is engaged, whereby during a rotation of the at least first and second bearing elements relative to each other, said rotation is inhibited by the frictional force produced by the brake device,
   wherein in the open state, the brake device is disengaged, whereby the at least first and second bearing elements are rotatable relative to each other without being inhibited by the brake device, and
   wherein the coupling device remains in the closed state in case the coupling device is not operated.

2. The bearing assembly according to claim 1, wherein the coupling device comprises:
   a gearing being aligned radially inside on one of the at least first and second bearing elements, and positioned on one of the at least first and second bearing elements, which is not clamped against the frictional element; and
   a corresponding gearing being aligned radially to an outside on the frictional element, wherein the gearings engage with each other in a closed state of the coupling device and are not engaged with each other in the open state of the coupling device.

3. The bearing assembly according to claim 2, wherein at least one of the gearings is arranged on a coupling element which is movable along a longitudinal direction.

4. The bearing assembly according to claim 1, wherein the coupling device comprises a transmission device by which a power for adjustment between the open state and the closed state may be transferred, or a pretension force of the clamping device may be transferred.

5. The bearing assembly according to claim 4, wherein the transmission device comprises two wedge elements which slide down on respective wedge faces thereof during adjustment.

6. The bearing assembly according to claim 1, wherein the clamping device is configured to permanently clamp the at least one frictional element against one of the at least first and second bearing elements by using an adjustable pretension force.

7. The bearing assembly according to claim 1, wherein the at least one clamping device comprises:

a split or an unsplit clamping collar;
a bent wire having a thread on both ends and being clamped by a clamping nut;
a steel rope which is hooked into a clamping element of the clamping device; and
a steel rope or a steel belt, which is clamped by a clamping element, which is annularly arranged around the bearing element, and is clamped to the clamping element on ends thereof.

8. The bearing assembly according to claim 1, wherein the bearing assembly comprises a casing, wherein the brake device or the coupling device is arranged outside of, or within, the casing.

9. The bearing assembly according to claim 1, wherein the coupling device comprises an electromagnetic actuator.

10. The bearing assembly according to claim 1, wherein the coupling device remains in the closed state in case it is not operated when the coupling device is pretensioned by a spring element (40) in the closed state.

11. A bearing assembly comprising at least one first bearing element and one second bearing element which are rotatably coupled relative to each other along a longitudinal axis, wherein the bearing assembly comprises:
a brake device, which inhibits relative rotation of the at least first and second bearing elements to each other by a frictional force produced by the brake device, wherein the brake device has at least one frictional element and at least one clamping device by which the frictional element is permanently clamped against one of the at least first and second bearing elements, and
a coupling device which is adjustable between an open state and a closed state,
wherein in the closed state the brake device is engaged, whereby during a rotation of the at least first and second bearing elements relative to each other, said rotation is inhibited by the frictional force produced by the brake device,
wherein in the open state, the brake device is disengaged, whereby the at least first and second bearing elements are rotatable relative to each other without being inhibited by the brake device, and
wherein the coupling device comprises:
a gearing being aligned radially inside on one of the at least first and second bearing elements, and positioned on one of the at least first and second bearing elements, which is not clamped against the frictional element; and
a corresponding gearing being aligned radially to an outside on the frictional element, wherein the gearings engage with each other in a closed state of the coupling device and are not engaged with each other in the open state of the coupling device.

12. The bearing assembly according to claim 11, wherein at least one of the gearings is arranged on a coupling element which is movable along a longitudinal direction.

13. A bearing assembly comprising at least one first bearing element and one second bearing element which are rotatably coupled relative to each other along a longitudinal axis, wherein the bearing assembly comprises:
a brake device, which inhibits relative rotation of the at least first and second bearing elements to each other by a frictional force produced by the brake device, wherein the brake device has at least one frictional element and at least one clamping device by which the frictional element is permanently clamped against one of the at least first and second bearing elements, and
a coupling device which is adjustable between an open state and a closed state,
wherein in the closed state the brake device is engaged, whereby during a rotation of the at least first and second bearing elements relative to each other, said rotation is inhibited by the frictional force produced by the brake device,
wherein in the open state, the brake device is disengaged, whereby the at least first and second bearing elements are rotatable relative to each other without being inhibited by the brake device, and
wherein the at least one clamping device comprises:
a split or an unsplit clamping collar;
a bent wire having a thread on both ends and being clamped by a clamping nut;
a steel rope which is hooked into a clamping element of the clamping device; and
a steel rope or a steel belt, which is clamped by a clamping element, which is annularly arranged around the bearing element, and is clamped to the clamping element on ends thereof.

\* \* \* \* \*